(12) United States Patent
Ma et al.

(10) Patent No.: US 10,143,422 B2
(45) Date of Patent: Dec. 4, 2018

(54) WIRELESS COMMUNICATION METHOD, WEARABLE DEVICE, MOBILE TERMINAL, AND SYSTEM

(71) Applicant: ZTE CORPORATION, Shenzhen, Guangdong Province (CN)

(72) Inventors: Kai Ma, Shenzhen (CN); Xiuli Hu, Shenzhen (CN); Bin Chen, Shenzhen (CN); Jiaojiao Xu, Shenzhen (CN)

(73) Assignee: XI'AN ZHONGXING NEW SOFTWARE CO., LTD., Xi'An, Shaanxi (CN)

( * ) Notice: Subject to any disclaimer, the term of this patent is extended or adjusted under 35 U.S.C. 154(b) by 0 days.

(21) Appl. No.: 15/526,339

(22) PCT Filed: May 20, 2015

(86) PCT No.: PCT/CN2015/079400
§ 371 (c)(1),
(2) Date: May 12, 2017

(87) PCT Pub. No.: WO2016/074464
PCT Pub. Date: May 19, 2016

(65) Prior Publication Data
US 2017/0319135 A1 Nov. 9, 2017

(30) Foreign Application Priority Data
Nov. 12, 2014 (CN) .......................... 2014 1 0635603

(51) Int. Cl.
*H04B 7/15* (2006.01)
*A61B 5/00* (2006.01)
(Continued)

(52) U.S. Cl.
CPC ............. *A61B 5/6831* (2013.01); *H03G 3/30* (2013.01); *H04B 1/0017* (2013.01);
(Continued)

(58) Field of Classification Search
CPC ...... A61B 5/6831; H03G 3/30; H04B 1/0017; H04W 16/14; H04W 72/00; H04W 88/06
See application file for complete search history.

(56) References Cited

U.S. PATENT DOCUMENTS 9,722,759 B2 * 8/2017 Shin ..................... H04L 5/0069
2014/0308930 A1 10/2014 Tran

FOREIGN PATENT DOCUMENTS

CN 1734833 A 2/2006
CN 102412858 A 4/2012
(Continued)

*Primary Examiner* — Nguyen T Vo
(74) *Attorney, Agent, or Firm* — Ling Wu; Stephen Yang; Ling & Yang Intellectual Property (57) ABSTRACT

A wireless communication method, a wearable device, a mobile terminal, and a system are provided. In the technical solution of the present disclosure, a mobile terminal sends frequency band information to a wearable device; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved.

20 Claims, 5 Drawing Sheets

(51) Int. Cl.
  *H04W 16/14* (2009.01)
  *H04W 72/00* (2009.01)
  *H04W 88/06* (2009.01)
  *H03G 3/30* (2006.01)
  *H04B 1/00* (2006.01)

(52) U.S. Cl.
  CPC .......... *H04W 16/14* (2013.01); *H04W 72/00* (2013.01); *H04W 88/06* (2013.01)

(56) References Cited

FOREIGN PATENT DOCUMENTS

| | | |
|---|---|---|
| CN | 103491217 A | 1/2014 |
| CN | 103718476 A | 4/2014 |
| CN | 103781202 A | 5/2014 |
| EP | 2169847 A2 | 3/2010 |
| EP | 3099138 A1 | 11/2016 |
| JP | 2002125256 A | 4/2002 |
| KR | 20110090831 A | 8/2011 |
| KR | 20120049338 A | 5/2012 |

\* cited by examiner

WIRELESS COMMUNICATION METHOD, WEARABLE DEVICE, MOBILE TERMINAL, AND SYSTEM

TECHNICAL FIELD

The document relates to the field of wireless communications, and more particularly to a wireless communication method, a wearable device, a mobile terminal, and a system.

BACKGROUND

Recently, wearable devices are rapidly developing, and various portable wearable devices including smart bracelet, smart watches and Google project glasses are becoming new favorites in the field of mobile communication terminals. Main functions of the smart wristbands on the market are to perform pulse detection, temperature detection, Global Positioning System (GPS) coordinate determination and the like on a human body by means of various sensors and communication systems such as GPSs, Bluetooth and Wireless Fidelity (WIFI), and feed information back to a mobile phone or pad for data processing. Functions of the smart watches are similar to those of the smart wristbands. At present, there are few users for smart glasses such as Google project glasses, which have powerful functions and may cover main functions of the mobile phones. In the near future, the wearable devices will become necessities of most people, and people will more view smart watch screens or smart glass screens, and demands for the mobile phones are gradually reduced.

In addition, with the rapid development of 4G, mobile phones have entered the age of 4G. At present, supporting multi-mode and multi-frequency by 4G mobile phones has become necessary conditions for warehousing of various operators. Many mobile phones support 5-mode and support 18-frequency bands. However, the performances of broadband and multiband antennae are poor due to space limitation of mobile phones, and diversity reception adopted in the solution is difficult to achieve better effect due to complexity of space and environment.

SUMMARY

The embodiment of the present disclosure is mainly intended to provide a wireless communication method, to solve the problem how to improve a capability of a mobile terminal receiving the base station data.

To this aim, the technical solution is adopted as follows.

A wireless communication method is provided. The method includes:

a wearable device receives frequency band information sent by a mobile terminal, herein the frequency band information includes a frequency band used during communication of the mobile terminal;

the wearable device receives a signal that is sent by a base station and corresponds to the frequency band information, and sends the signal to the mobile terminal;

the mobile terminal receives the signal, and receives a signal that is sent by the base station and corresponds to the frequency band information; and the mobile terminal acquires a radio signal corresponding to the frequency band information according to the signal that is sent by the wearable device and corresponds to the frequency band information and the signal that is sent by the base station and corresponds to the frequency band information.

In an exemplary embodiment, the step that the wearable device receives a signal that is sent by a base station and corresponds to the frequency band information and sends the signal to the mobile terminal includes:

the wearable device receives a first signal that is sent by the base station and corresponds to the frequency band information, converts the first signal into a first baseband signal, and after performing up conversion on the first baseband signal through a WIFI transceiving module, sends to the mobile terminal.

The step that the mobile terminal acquires a radio signal corresponding to the frequency band information according to the signal that is sent by the wearable device and corresponds to the frequency band information and the signal that is sent by the base station and corresponds to the frequency band information includes:

the mobile terminal receives a second signal sent by the wearable device, and converts the second signal into a second baseband signal.

The step that the mobile terminal receives the signal and receives a signal that is sent by the base station and corresponds to the frequency band information includes:

the mobile terminal converts a received third signal that is sent by the base station and corresponds to the frequency band information into a third baseband signal.

The step that the mobile terminal acquires a radio signal corresponding to the frequency band information according to the signal that is sent by the wearable device and corresponds to the frequency band information and the signal that is sent by the base station and corresponds to the frequency band information includes:

the mobile terminal acquires the radio signal corresponding to the frequency band information according to the second baseband signal and the third baseband signal, herein the second signal is a signal obtained after the first baseband signal is performed up conversion to be transmitted by the wearable device.

In an exemplary embodiment, the step that the wearable device converts the first signal into a first baseband signal, and after performing up conversion on the first baseband signal through a WIFI transceiving module, sends to the mobile terminal includes:

the wearable device amplifies the first signal, and then performs mixing through a mixer and a Local Oscillator (LO) to obtain the first baseband signal, performs signal processing on the first baseband signal, and then wirelessly transmits processed signal to the mobile terminal.

In an exemplary embodiment, the step that the mobile terminal converts the second signal into a second baseband signal includes:

the mobile terminal filters and amplifies the second signal, and then recovers the second signal into the second baseband signal, herein the second baseband signal is identical to or similar to the first baseband signal.

A wireless communication method is provided. The method includes:

receiving frequency band information sent by a mobile terminal, herein the frequency band information includes a frequency band used during communication of the mobile terminal; and receiving a signal that is sent by a base station and corresponds to the frequency band information, and sending the signal to the mobile terminal.

In an exemplary embodiment, the step of receiving a signal that is sent by a base station and corresponds to the frequency band information and sending the signal to the mobile terminal includes:

receiving a first signal that is sent by the base station and corresponds to the frequency band information, converting the first signal into a first baseband signal, and after performing up conversion on the first baseband signal through a WIFI transceiving module, sending to the mobile terminal.

In an exemplary embodiment, the step of converting the first signal into a first baseband signal and after performing up conversion on the first baseband signal through a WIFI transceiving module, sending to the mobile terminal includes:

amplifying the first signal, and then performing mixing through a mixer and an LO to obtain the first baseband signal, performing signal processing on the first baseband signal, and then wirelessly transmitting processed signal to the mobile terminal.

A wireless communication method is provided. The method includes:

sending frequency band information to a wearable device, herein the frequency band information includes a frequency band used during communication of the mobile terminal;

receiving a signal, and receiving a signal that is sent by a base station and corresponds to the frequency band information; and acquiring a radio signal corresponding to the frequency band information according to the signal that is sent by the wearable device and corresponds to the frequency band information and the signal that is sent by the base station and corresponds to the frequency band information.

In an exemplary embodiment, the step of acquiring a radio signal corresponding to the frequency band information according to the signal that is sent by the wearable device and corresponds to the frequency band information and the signal that is sent by the base station and corresponds to the frequency band information includes:

receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, herein the second signal is a signal obtained after the first baseband signal is performed up conversion to be transmitted by the wearable device.

In an exemplary embodiment, the step of converting the second signal into a second baseband signal includes:

filtering and amplifying the second signal, and then recovering the second signal into the second baseband signal, herein the second baseband signal is identical to or similar to the first baseband signal.

A wearable device is provided. The wearable device includes a first receiving unit, a second receiving unit and a sending unit.

The first receiving unit is configured to receive frequency band information sent by a mobile terminal, herein the frequency band information includes a frequency band used during communication of the mobile terminal.

The second receiving unit is configured to receive a signal that is sent by a base station and corresponds to the frequency band information.

The sending unit is configured to send the signal to the mobile terminal.

In an exemplary embodiment, the wearable device further includes a converting unit, and herein the second receiving unit is configured to receive a first signal that is sent by a base station and corresponds to the frequency band information;

the converting unit is configured to convert the first signal into a first baseband signal; and the sending unit is configured to perform up conversion on the first baseband signal to send to the mobile terminal.

In an exemplary embodiment, the converting unit is configured to convert the first signal into a first baseband signal in the following manner:

amplifying the first signal, and then performing mixing through a mixer and an LO to obtain the first baseband signal, performing signal processing on the first baseband signal, and then wirelessly transmitting processed signal to the mobile terminal.

A mobile terminal is provided. The mobile terminal includes a sending unit, a receiving unit and an acquiring unit.

The sending unit is configured to send frequency band information to a wearable device, herein the frequency band information includes a frequency band used during communication of the mobile terminal.

The receiving unit is configured to receive a signal, and receive a signal that is sent by a base station and corresponds to the frequency band information.

The acquiring unit is configured to acquire a radio signal corresponding to the frequency band information according to the signal that is sent by the wearable device and corresponds to the frequency band information and the signal that is sent by the base station and corresponds to the frequency band information.

In an exemplary embodiment, the acquiring unit is configured to acquire a radio signal corresponding to the frequency band information according to the signal that is sent by the wearable device and corresponds to the frequency band information and the signal that is sent by the base station and corresponds to the frequency band information in the following manner:

receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, herein the second signal is a signal obtained after the first baseband signal is performed up conversion to be transmitted by the wearable device.

In an exemplary embodiment, the acquiring unit is configured to convert the second signal into a second baseband signal in the following manner:

filtering and amplifying the second signal, and then recovering the second signal into the second baseband signal, herein the second baseband signal is identical to or similar to the first baseband signal.

A wireless communication system is provided. The system includes a mobile terminal and at least one wearable device.

The wearable device is configured to, receive frequency band information sent by the mobile terminal, herein the frequency band information includes a frequency band used during communication of the mobile terminal; and receive a signal that is sent by a base station and corresponds to the frequency band information, and send the signal to the mobile terminal.

The mobile terminal is configured to, send frequency band information to the wearable device, herein the frequency band information at least includes a frequency band used during communication of the mobile terminal; receive a signal, and receive a signal that is sent by the base station and corresponds to the frequency band information; and acquire a radio signal corresponding to the frequency band information according to the signal that is sent by the wearable device and corresponds to the frequency band information and the signal that is sent by the base station and corresponds to the frequency band information.

In an exemplary embodiment, the wearable device is configured to receive a signal that is sent by a base station and corresponds to the frequency band information, and send the signal to the mobile terminal in the following manner:

receiving a first signal that is sent by the base station and corresponds to the frequency band information, converting the first signal into a first baseband signal, and after performing up conversion on the first baseband signal through a WIFI transceiving module, sending to the mobile terminal.

In an exemplary embodiment, the wearable device is configured to convert the first signal into a first baseband signal, and after performing up conversion on the first baseband signal through a WIFI transceiving module, send to the mobile terminal in the following manner:

amplifying the first signal, and then performing mixing through a mixer and an LO to obtain the first baseband signal, performing signal processing on the first baseband signal, and then wirelessly transmitting processed signal to the mobile terminal.

In an exemplary embodiment, the mobile terminal is configured to acquire a radio signal corresponding to the frequency band information according to the signal that is sent by the wearable device and corresponds to the frequency band information and the signal that is sent by the base station and corresponds to the frequency band information in the following manner:

receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, herein the second signal is a signal obtained after the first baseband signal is performed up conversion to be transmitted by the wearable device.

In an exemplary embodiment, the mobile terminal is configured to convert the second signal into a second baseband signal in the following manner:

filtering and amplifying, by the mobile terminal, the second signal, and then recovering the second signal into the second baseband signal, herein the second baseband signal is identical to or similar to the first baseband signal.

Embodiments of the present disclosure provide a wireless communication method, a wearable device, a mobile terminal, a system, a computer program, and a carrier thereof. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network.

The purpose fulfillment, functional features and advantages of the present disclosure will be further described with reference to the accompanying drawings with embodiments.

DETAILED DESCRIPTION

It will be appreciated that specific embodiments described herein are merely used to explain the present disclosure without limiting the present disclosure.

An embodiment of the present disclosure provides a wireless communication method.

Figure 1:
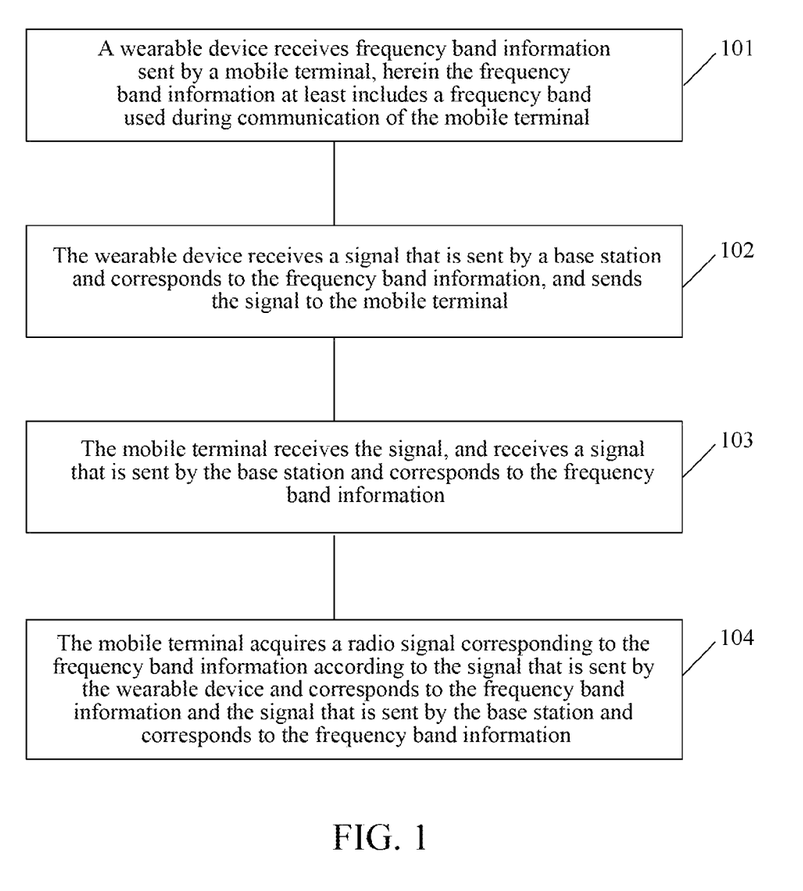
FIG. 1 is a flowchart of a first embodiment for a wireless communication method of the present disclosure.

Referring to FIG. 1, FIG. 1 is a flowchart of a first embodiment for a wireless communication method of the present disclosure.

In the first embodiment, the wireless communication method includes the following steps 101-104.

In step 101, a wearable device receives frequency band information sent by a mobile terminal, herein the frequency band information at least includes a frequency band used during communication of the mobile terminal.

Figure 2:
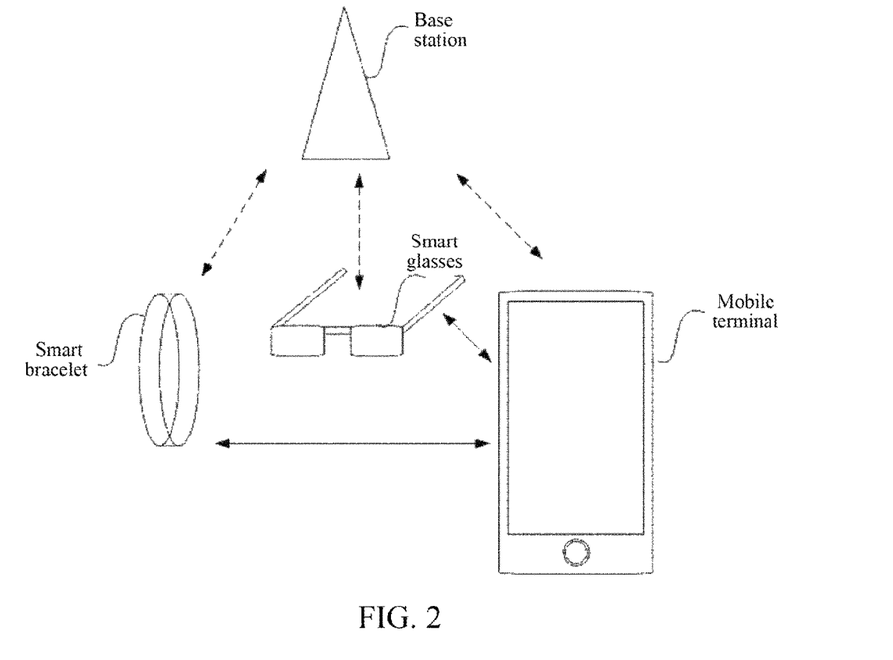
FIG. 2 is a schematic diagram of a wireless communication scenario according to an embodiment of the present disclosure.

Specifically, referring to FIG. 2, FIG. 2 is a schematic diagram of a wireless communication scenario according to an embodiment of the present disclosure. A mobile phone terminal and one or more wearable devices confirm a connecting state, and acquire a communication system supported by the one or more wearable devices and a specific frequency band of the supported communication system. The mobile phone terminal sends frequency band information, currently used for communicating, to the one or more wearable devices.

In step 102, the wearable device receives a signal that is sent by a base station and corresponds to the frequency band information, and sends the signal to the mobile terminal.

Specifically, the wearable device has a communication receiving module, and is capable of receiving the signal from the base station. Furthermore, multiple wearable devices and the mobile phone terminal may be interconnected in a short-distance communication mode (WIFI, BT, etc.), to form a multipoint-to-multipoint composite network architecture, thus greatly improving the receiving capability of the mobile phone terminal.

In an exemplary embodiment, that the wearable device receives a signal that is sent by a base station and corresponds to the frequency band information and sends the signal to the mobile terminal includes:

the wearable device receives a first signal that is sent by a base station and corresponds to the frequency band information, converts the first signal into a first baseband signal, and after performing up conversion on the first baseband signal through a WIFI transceiving module, sends to the mobile terminal.

In an exemplary embodiment, that the wearable device converts the first signal into a first baseband signal, and after performing up conversion on the first baseband signal through a WIFI transceiving module, sends to the mobile terminal includes:

the wearable device amplifies the first signal, and then performs mixing through a mixer and an LO to obtain the first baseband signal, and performs signal processing on the first baseband signal, and then wirelessly transmits processed signal to the mobile terminal.

Figure 3:
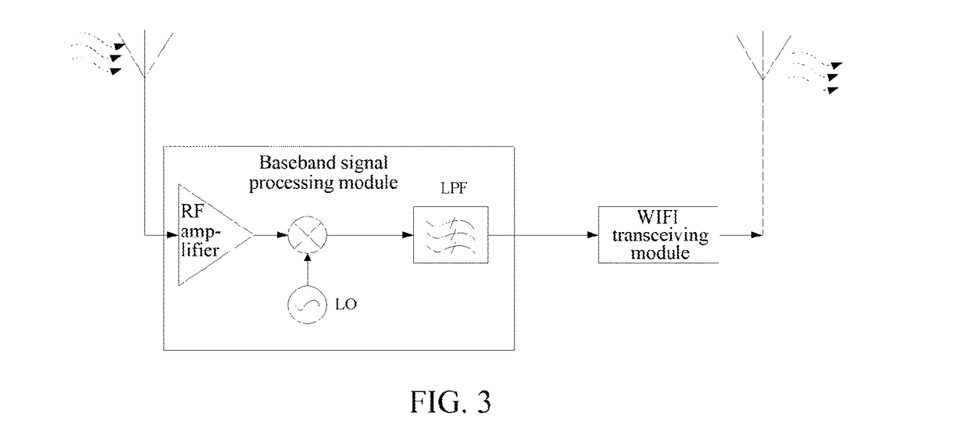
FIG. 3 is a structural diagram of a wearable device according to an embodiment of the present disclosure.

Specifically, referring to FIG. 3, FIG. 3 is a structural diagram of a wearable device according to an embodiment of the present disclosure. The wearable device includes an RF amplifier, an LO, a Low-Pass Filter (LPF), a baseband signal processing module, and a WIFI transceiving module. The baseband signal processing module includes the RF amplifier, the LO and the LPF. The baseband signal processing module is configure to convert the received signal sent by the base station into a first baseband signal. The WIFI transceiving module is configured to perform up conversion on the first baseband signal to send to the mobile terminal. The wearable device receives a signal through a receiving antenna, amplifies a high-frequency signal, and then performs mixing with a signal of the LO through the mixer to obtain a baseband signal, and filters the baseband signal. The filtered baseband signal enters the WIFI transceiving module, and is processed, and then enters a transmitting antenna for sending through the WIFI transceiving module.

In step 103, the mobile terminal receives the signal, and receives the signal that is sent by the base station and corresponds to the frequency band information.

In step 104, the mobile terminal acquires a radio signal corresponding to the frequency band information according to the signal that is sent by the wearable device and corresponds to the frequency band information and the signal that is sent by the base station and corresponds to the frequency band information.

In an exemplary embodiment, that the mobile terminal acquires a radio signal corresponding to the frequency band information according to the signal that is sent by the wearable device and corresponds to the frequency band information and the signal that is sent by the base station and corresponds to the frequency band information includes:

the mobile terminal receives a second signal sent by the wearable device, and converts the second signal into a second baseband signal; the mobile terminal converts a received third signal that is sent by the base station and corresponds to the frequency band information into a third baseband signal; and the mobile terminal acquires a radio signal corresponding to the frequency band information according to the second baseband signal and the third baseband signal, herein the second signal is a signal obtained after the first baseband signal is performed up conversion to be transmitted by the wearable device.

Herein, the second baseband signal and the first baseband signal may be identical or different.

In an exemplary embodiment, that the mobile terminal converts the second signal into a second baseband signal includes:

the mobile terminal filters and amplifies the second signal, and then recovers the second signal into the second baseband signal.

Figure 4:
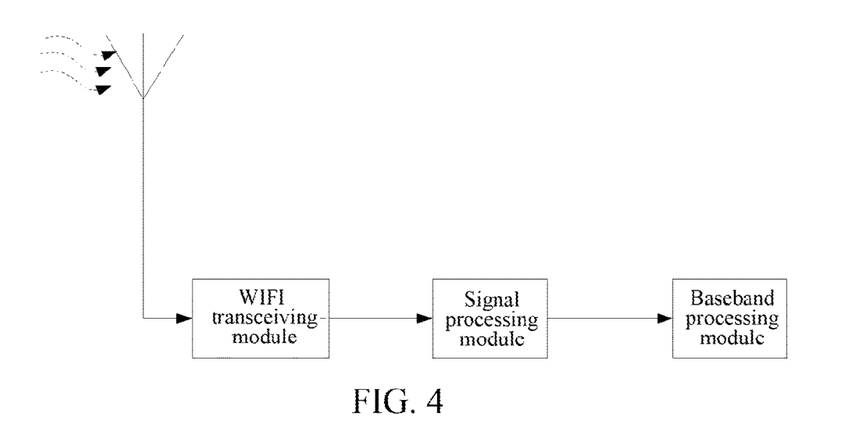
FIG. 4 is a structural diagram of a mobile terminal according to an embodiment of the present disclosure.

Specifically, referring to FIG. 4, FIG. 4 is a structural diagram of a mobile terminal according to an embodiment of the present disclosure. The mobile terminal includes a WIFI transceiving module, a signal processing module and a baseband processing module. The signal processing module is configured to convert a signal into a second baseband signal, and the baseband processing module is configured to process the second baseband signal and the third baseband signal. A WIFI antenna receives a second signal sent by the wearable device, and the second signal is processed, such as filtered, amplified and the like, by the WIFI transceiving module, and then the processed signal is converted into a second baseband signal by the signal processing module. The mobile terminal converts a received third signal sent by the base station into a third baseband signal, and the second baseband signal and the third baseband signal are processed by the baseband processing module.

In the whole communication process, the wearable device plays a role as a diversity receiving module of the mobile phone. Due to natural advantages of the wearable device, an antenna environment and an antenna space make antenna performance excellent or even better than those of a communication antenna of the mobile phone terminal. The wearable device is used as a repeater due to these advantages. The wearable device may greatly improve the receiving performance of the mobile phone, and communication systems supported by the wearable device may be various systems, such as 2G/3G/4G, WIFI, BT, GPS and so on.

Embodiments of the present disclosure provide a wireless communication method, a wearable device, a mobile terminal, and a system. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network.

An embodiment of the present disclosure further provides a wireless communication method.

Figure 5:
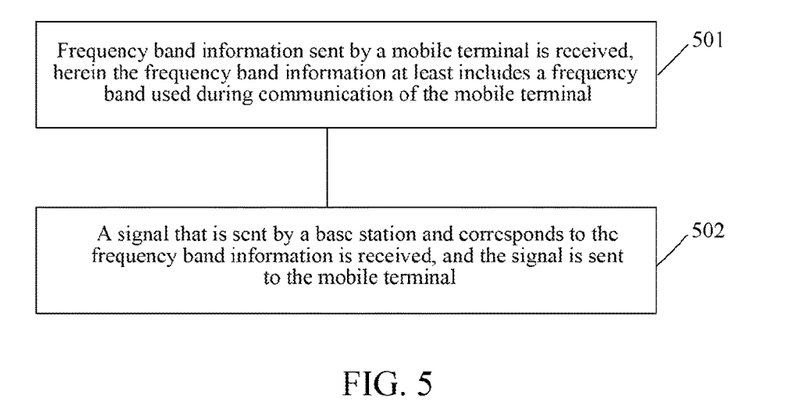
FIG. 5 is a flowchart of a second embodiment for a wireless communication method of the present disclosure.

Referring to FIG. 5, FIG. 5 is a flowchart of a second embodiment for a wireless communication method of the present disclosure.

In the second embodiment, the wireless communication method includes the steps 501-502 as follows.

In step 501, frequency band information sent by a mobile terminal is received; herein the frequency band information at least includes a frequency band used during communication of the mobile terminal.

In step 502, a signal that is sent by a base station and corresponds to the frequency band information is received, and the signal is sent to the mobile terminal.

In an exemplary embodiment, that a signal that is sent by a base station and corresponds to the frequency band information is received and the signal is sent to the mobile terminal includes:

receiving a first signal that is sent by a base station and corresponds to the frequency band information, converting the first signal into a first baseband signal, and after performing up conversion on the first baseband signal through a WIFI transceiving module, sending to the mobile terminal.

In an exemplary embodiment, converting the first signal into a first baseband signal and after performing up conversion on the first baseband signal through a WIFI transceiving module, sending to the mobile terminal includes:

amplifying the first signal, and then performing mixing through a mixer and an LO to obtain the first baseband signal, performing signal processing on the first baseband signal, and then wirelessly transmitting processed signal to the mobile terminal.

Specifically, referring to FIG. 3, FIG. 3 is a structural diagram of a wearable device according to an embodiment of the present disclosure. The wearable device receives a signal through a receiving antenna, amplifies a high-frequency signal, and then performs mixing with a signal of the LO through the mixer to obtain a baseband signal, and filters the baseband signal. The filtered baseband signal enters the WIFI transceiving module, and is processed, and then enters a transmitting antenna for sending through the WIFI transceiving module.

In the whole communication process, the wearable device plays a role as a diversity receiving module of a mobile phone. Due to natural advantages of the wearable device, an antenna environment and an antenna space make antenna performance excellent or even better than those of a communication antenna of the mobile phone terminal. The wearable device is used as a repeater due to these advantages. The wearable device may greatly improve the receiving performance of the mobile phone, and communication systems supported by the wearable device may be various systems, such as 2G/3G/4G, WIFI, BT, GPS and so on.

Embodiments of the present disclosure provide a wireless communication method, a wearable device, a mobile terminal, and a system. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network.

Another embodiment of the present disclosure further provides a wireless communication method.

Figure 6:
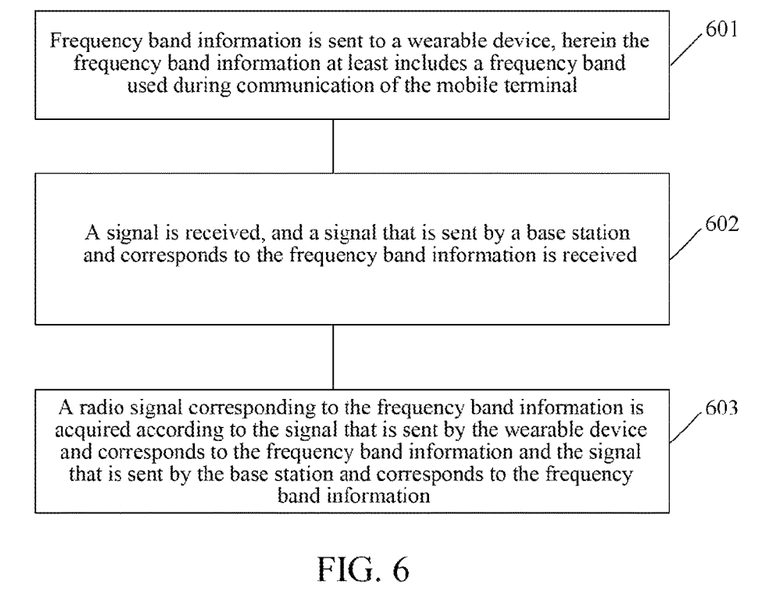
FIG. 6 is a flowchart of a third embodiment for a wireless communication method of the present disclosure.

Referring to FIG. 6, FIG. 6 is a flowchart of a third embodiment for a wireless communication method of the present disclosure.

In the third embodiment, the wireless communication method includes the steps 601-603 as follows.

In step 601, frequency band information is sent to a wearable device, herein the frequency band information at least includes a frequency band used during communication of the mobile terminal.

In step 602, a signal is received, and a signal that is sent by a base station and corresponds to the frequency band information is received.

In step 603, a radio signal corresponding to the frequency band information is acquired according to the signal that is sent by the wearable device and corresponds to the frequency band information and the signal that is sent by the base station and corresponds to the frequency band information.

In an exemplary embodiment, that a radio signal corresponding to the frequency band information is acquired according to the signal that is sent by the wearable device and corresponds to the frequency band information and the signal that is sent by the base station and corresponds to the frequency band information includes:

receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, herein the second signal is a signal obtained after the first baseband signal is performed up conversion to be transmitted by the wearable device.

In an exemplary embodiment, converting the second signal into a second baseband signal includes:

filtering and amplifying the second signal, and then recovering the second signal into the second baseband signal, herein the second baseband signal is identical to or similar to the first baseband signal.

Specifically, referring to FIG. 4, FIG. 4 is a structural diagram of a mobile terminal according to an embodiment of the present disclosure. A WIFI antenna receives a second signal sent by the wearable device, and the second signal is processed, such as filtered, amplified and the like, by a WIFI transceiving module, and then the processed signal is converted into a second baseband signal by a signal processing module. The mobile terminal converts a received third signal sent by the base station into a third baseband signal, and the second baseband signal and the third baseband signal are processed by a baseband processing module.

In the whole communication process, the wearable device plays a role as a diversity receiving module of the mobile phone. Due to natural advantages of the wearable device, an antenna environment and an antenna space make antenna performance excellent or even better than those of a communication antenna of the mobile phone terminal. The wearable device is used as a repeater due to these advantages. The wearable device may greatly improve the receiving performance of the mobile phone, and communication systems supported by the wearable device may be various systems, such as 2G/3G/4G, WIFI, BT, GPS and so on.

Embodiments of the present disclosure provide a wireless communication method, a wearable device, a mobile terminal, and a system. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network.

An embodiment of the present disclosure further provides a wearable device.

Figure 7:
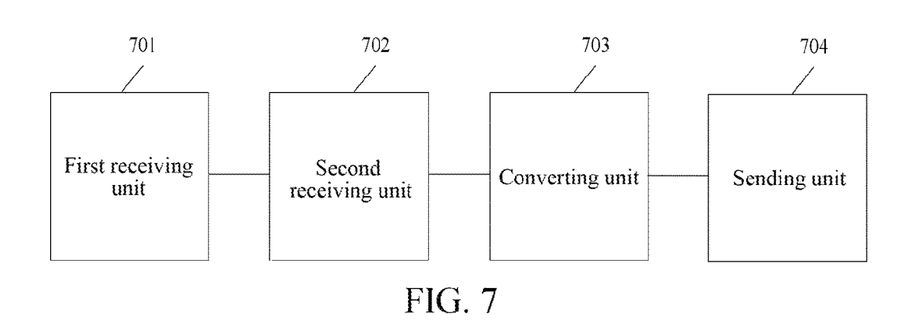
FIG. 7 is a functional module diagram of a first embodiment for a wearable device of the present disclosure.

Referring to FIG. 7, FIG. 7 is a functional module diagram of a first embodiment for a wearable device of the present disclosure. The wearable device includes a first receiving unit 701, a second receiving unit 702, a sending unit 703 and a converting unit 704.

The first receiving unit 701 is configured to receive frequency band information sent by a mobile terminal, herein the frequency band information at least includes a frequency band used during communication of the mobile terminal.

The second receiving unit 702 is configured to receive a signal that is sent by a base station and corresponds to the frequency band information.

The sending unit 703 is configured to send the signal to the mobile terminal.

In an exemplary embodiment, the wearable device further includes a converting unit 704, herein the second receiving unit 702 is configured to receive a first signal that is sent by a base station and corresponds to the frequency band information;

the converting unit 704 is configured to convert the first signal into a first baseband signal; and the sending unit 703 is configured to perform up conversion on the first baseband signal to send to the mobile terminal.

In an exemplary embodiment, the converting unit 704 is configured to, amplify the first signal, and then perform mixing through a mixer and an LO to obtain the first baseband signal, perform signal processing on the first baseband signal, and then wirelessly transmit processed signal to the mobile terminal.

Specifically, referring to FIG. 3, FIG. 3 is a structural diagram of a wearable device according to an embodiment of the present disclosure. The wearable device receives a signal through a receiving antenna, amplifies a high-frequency signal, and then performs mixing with a signal of the LO through the mixer to obtain a baseband signal, and filters the baseband signal. The filtered baseband signal enters the WIFI transceiving module, and is processed, and then enters a transmitting antenna for sending through the WIFI transceiving module.

In the whole communication process, the wearable device plays a role as a diversity receiving module of a mobile phone. Due to natural advantages of the wearable device, an antenna environment and an antenna space make antenna performance excellent or even better than those of a communication antenna of the mobile phone terminal. The wearable device is used as a repeater due to these advantages. The wearable device may greatly improve the receiving performance of the mobile phone, and communication systems supported by the wearable device may be various systems, such as 2G/3G/4G, WIFI, BT, GPS and so on.

Embodiments of the present disclosure provide a wireless communication method, a wearable device, a mobile terminal, and a system. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network.

An embodiment of the present disclosure further provides a mobile terminal.

Figure 8:
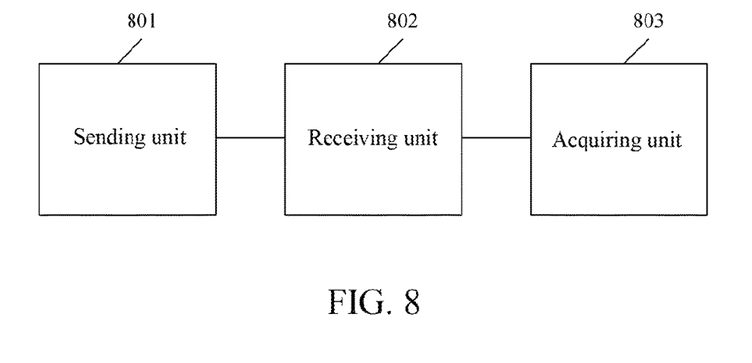
FIG. 8 is a functional module diagram of a first embodiment for a mobile terminal of the present disclosure.

Referring to FIG. 8, FIG. 8 is a functional module diagram of a first embodiment for a mobile terminal of the present disclosure. The mobile terminal includes a sending unit 801, a receiving unit 802 and an acquiring unit 803.

The sending unit 801 is configured to send frequency band information to a wearable device, herein the frequency band information includes a frequency band used during communication of the mobile terminal.

The receiving unit 802 is configured to receive a signal, and receive a signal that is sent by a base station and corresponds to the frequency band information.

The acquiring unit 803 is configured to acquire a radio signal corresponding to the frequency band information according to the signal that is sent by the wearable device and corresponds to the frequency band information and the signal that is sent by the base station and corresponds to the frequency band information.

In an exemplary embodiment, the acquiring unit 803 is configured to receive a second signal sent by the wearable device, and convert the second signal into a second baseband signal; convert a received third signal that is sent by the base station and corresponds to the frequency band information into a third baseband signal; and acquire a radio signal corresponding to the frequency band information according to the second baseband signal and the third baseband signal, herein the second signal is a signal obtained after the first baseband signal is performed up conversion to be transmitted by the wearable device.

Converting the second signal into a second baseband signal by the acquiring unit 803 includes:

filtering and amplifying the second signal, and then recovering the second signal into the second baseband signal, herein the second baseband signal is identical to or similar to the first baseband signal.

Specifically, referring to FIG. 4, FIG. 4 is a structural diagram of a mobile terminal according to an embodiment of the present disclosure. A WIFI antenna receives a second signal sent by the wearable device, and the second signal is processed, such as filtered, amplified and the like, by a WIFI transceiving module, and then the processed signal is converted into a second baseband signal by a signal processing module. The mobile terminal converts a received third signal sent by the base station into a third baseband signal, and the second baseband signal and the third baseband signal are processed by a baseband processing module.

In the whole communication process, the wearable device plays a role as a diversity receiving module of the mobile phone. Due to natural advantages of the wearable device, an antenna environment and an antenna space make antenna performance excellent or even better than those of a communication antenna of the mobile phone terminal. The wearable device is used as a repeater due to these advantages. The wearable device may greatly improve the receiving performance of the mobile phone, and communication systems supported by the wearable device may be various systems, such as 2G/3G/4G, WIFI, BT, GPS and so on.

Embodiments of the present disclosure provide a wireless communication method, a wearable device, a mobile terminal, and a system. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network.

An embodiment of the present disclosure further provides a system.

Figure 9:
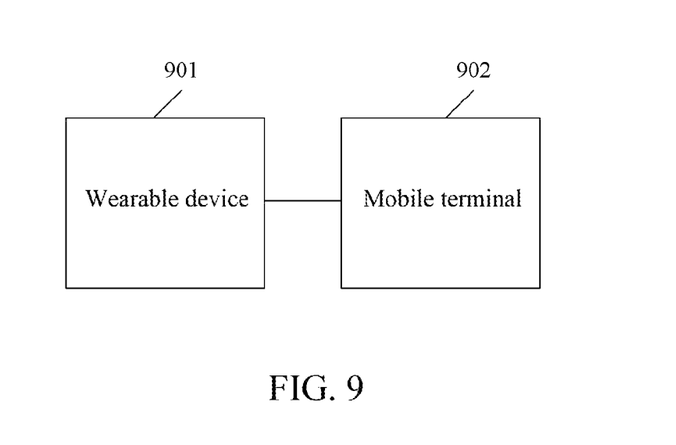
FIG. 9 is a system structure diagram of a first embodiment of the present disclosure.

Referring to FIG. 9, FIG. 9 is a system structure diagram of a first embodiment of the present disclosure. The system includes at least one wearable device 901 and a mobile terminal 902.

The wearable device 901 is configured to receive frequency band information sent by the mobile terminal, herein the frequency band information includes a frequency band used during communication of the mobile terminal; and receive a signal that is sent by a base station and corresponds to the frequency band information, and send the signal to the mobile terminal.

The mobile terminal 902 is configured to send frequency band information to the wearable device, herein the frequency band information includes a frequency band used during communication of the mobile terminal; receive a signal, and receive a signal that is sent by a base station and corresponds to the frequency band information; and acquire a radio signal corresponding to the frequency band information according to the signal that is sent by the wearable device and corresponds to the frequency band information and the signal that is sent by the base station and corresponds to the frequency band information.

In an exemplary embodiment, receiving, by the wearable device, a signal that is sent by a base station and corresponds to the frequency band information and sending the signal to the mobile terminal includes:

receiving a first signal that is sent by a base station and corresponds to the frequency band information, converting the first signal into a first baseband signal, and after performing up conversion on the first baseband signal through a WIFI transceiving module, sending to the mobile terminal.

In an exemplary embodiment, converting, by the wearable device, the first signal into a first baseband signal and after performing up conversion on the first baseband signal through a WIFI transceiving module, sending to the mobile terminal includes:

amplifying the first signal, and then performing mixing through a mixer and an LO to obtain the first baseband signal, performing signal processing on the first baseband signal, and then wirelessly transmitting processed signal to the mobile terminal.

Specifically, referring to FIG. 3, FIG. 3 is a structural diagram of a wearable device according to an embodiment of the present disclosure. The wearable device receives a signal through a receiving antenna, amplifies a high-frequency signal, and then performs mixing with a signal of the LO through the mixer to obtain a baseband signal, and filters the baseband signal. The filtered baseband signal enters the WIFI transceiving module, and is processed, and then enters a transmitting antenna for sending through the WIFI transceiving module.

In an exemplary embodiment, acquiring, by the mobile terminal, a radio signal corresponding to the frequency band information according to the signal that is sent by the wearable device and corresponds to the frequency band information and the signal that is sent by the base station and corresponds to the frequency band information includes:

receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, herein the second signal is a signal obtained after the first baseband signal is performed up conversion to be transmitted by the wearable device.

In an exemplary embodiment, that the mobile terminal converts the second signal into a second baseband signal includes:

the mobile terminal filters and amplifies the second signal, and then recovers the second signal into the second baseband signal, herein the second baseband signal is identical to or similar to the first baseband signal.

Specifically, referring to FIG. 4, FIG. 4 is a structural diagram of a mobile terminal according to an embodiment of the present disclosure. A WIFI antenna receives a second signal sent by the wearable device, the second signal is processed, such as filtered, amplified and the like, by a WIFI transceiving module, and then the processed signal is converted into a second baseband signal by a signal processing module. The mobile terminal converts a received third signal sent by the base station into a third baseband signal, and the second baseband signal and the third baseband signal are processed by a baseband processing module.

In the whole communication process, the wearable device plays a role as a diversity receiving module of the mobile phone. Due to natural advantages of the wearable device, an antenna environment and an antenna space make antenna performance excellent or even better than those of a communication antenna of the mobile phone terminal. The wearable device is used as a repeater due to these advantages. The wearable device may greatly improve the receiving performance of the mobile phone, and communication systems supported by the wearable device may be various systems, such as 2G/3G/4G, WIFI, BT, GPS and so on.

An embodiment of the present disclosure also discloses a computer program, including a program instruction. When the program instruction is executed by a wearable device, the wearable device can execute any one of the abovementioned wireless communication methods.

An embodiment of the present disclosure also discloses a carrier carrying the computer program.

The embodiment of the present disclosure also discloses a computer program, including a program instruction. When the program instruction is executed by a mobile terminal, the mobile terminal is enabled to execute any of the abovementioned wireless communication methods.

The embodiment of the present disclosure also discloses a carrier carrying the computer program.

Embodiments of the present disclosure provide a wireless communication method, a wearable device, a mobile terminal, a system, a computer program, and a carrier thereof. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network.

The above is only the preferable specific implementation modes of the present disclosure. However, the scope of protection of the present disclosure is not limited thereto. Variations or replacements easily conceivable to any person skilled in the technical art within the disclosed technical scope of the present disclosure shall fall within the scope of protection of the present disclosure. Therefore, the scope of protection of the present disclosure shall refer to the scope of protection of the claims.

INDUSTRIAL APPLICABILITY

Embodiments of the present disclosure provide a wireless communication method, a wearable device, a mobile terminal, and a system. According to the method, a mobile terminal sends frequency band information to a wearable device, herein the frequency band information at least includes a frequency band used during communication of the mobile terminal; the mobile terminal receives a second signal sent by the wearable device, converts the second signal into a second baseband signal, receives a third signal that is sent by a base station and corresponds to the frequency band information, and coverts the third signal into a third baseband signal; and the mobile terminal acquires a radio signal corresponding to the frequency band information according to the second baseband signal and the third baseband signal. In this way, data can be received through multiple paths by using communication capabilities of multiple wearable devices, and the receiving capability of a mobile phone can be greatly improved. In addition, the wearable device or other mobile terminals may also be used as final data processing terminals, and other mobile terminals may also be used as repeaters to join in a network. Therefore, the present disclosure has strong industrial practicality.

What is claimed is:

1. A wireless communication method, comprising:
   receiving, by a wearable device, frequency band information sent by a mobile terminal, wherein the frequency band information comprises a frequency band used during communication of the mobile terminal;
   receiving, by the wearable device, a signal that is sent by a base station and corresponds to the frequency band information, and sending the signal to the mobile terminal;
   receiving, by the mobile terminal, the signal, and receiving a signal that is sent by the base station and corresponds to the frequency band information; and
   acquiring, by the mobile terminal, a radio signal corresponding to the frequency band information according to the signal that is sent by the wearable device and corresponds to the frequency band information and the signal that is sent by the base station and corresponds to the frequency band information.

2. The wireless communication method according to claim 1, wherein
   the step of receiving, by the wearable device, a signal that is sent by a base station and corresponds to the frequency band information and sending the signal to the mobile terminal comprises:
   receiving, by the wearable device, a first signal that is sent by the base station and corresponds to the frequency band information, converting the first signal into a first baseband signal, and after performing up conversion on the first baseband signal through a WIFI transceiving module, sending to the mobile terminal;
   the step of acquiring, by the mobile terminal, a radio signal corresponding to the frequency band information according to the signal that is sent by the wearable device and corresponds to the frequency band information and the signal that is sent by the base station and corresponds to the frequency band information comprises:
   receiving, by the mobile terminal, a second signal sent by the wearable device, and converting the second signal into a second baseband signal;
   the step of receiving, by the mobile terminal, the signal and receiving a signal that is sent by the base station and corresponds to the frequency band information comprises:
   converting, by the mobile terminal, a received third signal that is sent by the base station and corresponds to the frequency band information into a third baseband signal; and
   the step of acquiring, by the mobile terminal, a radio signal corresponding to the frequency band information according to the signal that is sent by the wearable device and corresponds to the frequency band information and the signal that is sent by the base station and corresponds to the frequency band information comprises:
   acquiring, by the mobile terminal, the radio signal corresponding to the frequency band information according to the second baseband signal and the third baseband signal, wherein the second signal is a signal obtained after the first baseband signal is performed up conversion to be transmitted by the wearable device.

3. The wireless communication method according to claim 2, wherein the step of converting, by the wearable device, the first signal into a first baseband signal and after performing up conversion on the first baseband signal through a WIFI transceiving module, sending to the mobile terminal comprises:
amplifying, by the wearable device, the first signal, and then performing mixing through a mixer and a Local Oscillator, LO, to obtain the first baseband signal; performing signal processing on the first baseband signal, and then wirelessly transmitting processed signal to the mobile terminal.

4. The wireless communication method according to claim 2, wherein the step of converting, by the mobile terminal, the second signal into a second baseband signal comprises:
filtering and amplifying, by the mobile terminal, the second signal, and then recovering the second signal into the second baseband signal, wherein the second baseband signal is identical to or similar to the first baseband signal.

5. A wireless communication method, comprising:
receiving frequency band information sent by a mobile terminal, wherein the frequency band information comprises a frequency band used during communication of the mobile terminal; and
receiving a signal that is sent by a base station and corresponds to the frequency band information, and sending the signal to the mobile terminal.

6. The wireless communication method according to claim 5, wherein the step of receiving a signal that is sent by a base station and corresponds to the frequency band information and sending the signal to the mobile terminal comprises:
receiving a first signal that is sent by the base station and corresponds to the frequency band information, converting the first signal into a first baseband signal, and after performing up conversion on the first baseband signal through a WIFI transceiving module, sending to the mobile terminal.

7. The wireless communication method according to claim 6, wherein the step of converting the first signal into a first baseband signal and after performing up conversion on the first baseband signal through a WIFI transceiving module, sending to the mobile terminal comprises:
amplifying the first signal, and then performing mixing through a mixer and a Local Oscillator, LO, to obtain the first baseband signal, performing signal processing on the first baseband signal, and then wirelessly transmitting processed signal to the mobile terminal.

8. A wireless communication method, comprising:
sending frequency band information to a wearable device, wherein the frequency band information comprises a frequency band used during communication of the mobile terminal;
receiving a signal that is sent by the wearable device and corresponds to the frequency band information, and receiving a signal that is sent by a base station and corresponds to the frequency band information; and
acquiring a radio signal corresponding to the frequency band information according to the signal that is sent by the wearable device and corresponds to the frequency band information and the signal that is sent by the base station and corresponds to the frequency band information.

9. The wireless communication method according to claim 8, wherein the step of acquiring a radio signal corresponding to the frequency band information according to the signal that is sent by the wearable device and corresponds to the frequency band information and the signal that is sent by the base station and corresponds to the frequency band information comprises:
receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, wherein the second signal is a signal obtained after the first baseband signal is performed up conversion to be transmitted by the wearable device.

10. The wireless communication method according to claim 9, wherein the step of converting the second signal into a second baseband signal comprises:
filtering and amplifying the second signal, and then recovering the second signal into the second baseband signal, wherein the second baseband signal is identical to or similar to the first baseband signal.

11. A mobile terminal implementing the wireless communication method according to claim 8, comprising a sending unit, a receiving unit and an acquiring unit, wherein
the sending unit is configured to send frequency band information to a wearable device, wherein the frequency band information comprises a frequency band used during communication of the mobile terminal;
the receiving unit is configured to receive a signal that is sent by the wearable device and corresponds to the frequency band information, and receive a signal that is sent by a base station and corresponds to the frequency band information; and
the acquiring unit is configured to acquire a radio signal corresponding to the frequency band information according to the signal that is sent by the wearable device and corresponds to the frequency band information and the signal that is sent by the base station and corresponds to the frequency band information.

12. The mobile terminal according to claim 11, wherein the acquiring unit is configured to acquire a radio signal corresponding to the frequency band information according to the signal that is sent by the wearable device and corresponds to the frequency band information and the signal that is sent by the base station and corresponds to the frequency band information in the following manner:
receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, wherein the second signal is a signal obtained after the first baseband signal is performed up conversion to be transmitted by the wearable device.

13. The mobile terminal according to claim 12, wherein the acquiring unit is configured to convert the second signal into a second baseband signal in the following manner:
filtering and amplifying the second signal, and then recovering the second signal into the second baseband signal, wherein the second baseband signal is identical to or similar to the first baseband signal.

14. A wireless communication system, comprising the mobile terminal according to claim 11 and at least one wearable device, wherein
the wearable device is configured to, receive frequency band information sent by the mobile terminal, wherein the frequency band information comprises a frequency band used during communication of the mobile terminal; and receive a signal that is sent by a base station and corresponds to the frequency band information, and send the signal to the mobile terminal; and
the mobile terminal is configured to, send frequency band information to the wearable device, wherein the frequency band information at least comprises a frequency band used during communication of the mobile terminal; receive a signal, and receive a signal that is sent by the base station and corresponds to the frequency band information; and acquire a radio signal corresponding to the frequency band information according to the signal that is sent by the wearable device and corresponds to the frequency band information and the signal that is sent by the base station and corresponds to the frequency band information.

15. The wireless communication system according to claim 14, wherein the wearable device is configured to receive a signal that is sent by a base station and corresponds to the frequency band information, and send the signal to the mobile terminal in the following manner:
receiving a first signal that is sent by the base station and corresponds to the frequency band information, converting the first signal into a first baseband signal, and after performing up conversion on the first baseband signal through a WIFI transceiving module, sending to the mobile terminal.

16. The wireless communication system according to claim 15, wherein the wearable device is configured to convert the first signal into a first baseband signal, and after performing up conversion on the first baseband signal through a WIFI transceiving module, send to the mobile terminal in the following manner:
amplifying the first signal, and then performing mixing through a mixer and a Local Oscillator, LO, to obtain the first baseband signal; performing signal processing on the first baseband signal, and then wirelessly transmitting processed signal to the mobile terminal.

17. The wireless communication system according to claim 14, wherein the mobile terminal is configured to acquire a radio signal corresponding to the frequency band information according to the signal that is sent by the wearable device and corresponds to the frequency band information and the signal that is sent by the base station and corresponds to the frequency band information in the following manner:
receiving a second signal sent by the wearable device, and converting the second signal into a second baseband signal; converting a received third signal that is sent by the base station and corresponds to the frequency band information into a third baseband signal; and acquiring a radio signal corresponding to the frequency band information according to the second baseband signal and the third baseband signal, wherein the second signal is a signal obtained after the first baseband signal is performed up conversion to be transmitted by the wearable device;
and
wherein the mobile terminal is configured to convert the second signal into a second baseband signal in the following manner:
filtering and amplifying, by the mobile terminal, the second signal, and then recovering the second signal into the second baseband signal, wherein the second baseband signal is identical to or similar to the first baseband signal.

18. A wearable device, comprising a first receiving unit, a second receiving unit and a sending unit, wherein
the first receiving unit is configured to receive frequency band information sent by a mobile terminal, wherein the frequency band information comprises a frequency band used during communication of the mobile terminal;
the second receiving unit is configured to receive a signal that is sent by a base station and corresponds to the frequency band information; and
the sending unit is configured to send the signal to the mobile terminal.

19. The wearable device according to claim 18, wherein the wearable device further comprises a converting unit, wherein
the second receiving unit is configured to receive a first signal that is sent by the base station and corresponds to the frequency band information;
the converting unit is configured to convert the first signal into a first baseband signal; and
the sending unit is configured to perform up conversion on the first baseband signal to send to the mobile terminal.

20. The wearable device according to claim 19, wherein the converting unit is configured to convert the first signal into a first baseband signal in the following manner:
amplifying the first signal, and then performing mixing through a mixer and a Local Oscillator, LO, to obtain the first baseband signal; performing signal processing on the first baseband signal, and then wirelessly transmitting processed signal to the mobile terminal.

* * * * *